United States Patent [19]
Vesely

[11] Patent Number: 5,868,673
[45] Date of Patent: Feb. 9, 1999

[54] SYSTEM FOR CARRYING OUT SURGERY, BIOPSY AND ABLATION OF A TUMOR OR OTHER PHYSICAL ANOMALY

[75] Inventor: Ivan Vesely, Cleveland Heights, Ohio

[73] Assignee: Sonometrics Corporation, London, Ontario, Canada

[21] Appl. No.: 815,141

[22] Filed: Mar. 11, 1997

Related U.S. Application Data

[63] Continuation-in-part of Ser. No. 411,959, which is a continuation-in-part of PCT/CA96/00194 Mar. 26, 1996, Pat. No. 5,515,853.

[51] Int. Cl.$^6$ ...................................................... A61B 6/00
[52] U.S. Cl. ........................... 600/407; 600/461; 606/130
[58] Field of Search ..................................... 600/407, 414, 600/417, 439, 437, 461; 128/915, 916, 920, 899; 378/37, 205; 606/130; 601/2, 3

[56] References Cited

U.S. PATENT DOCUMENTS

| | | |
|---|---|---|
| 4,173,228 | 11/1979 | VanSteenwyk et al. . |
| 4,304,239 | 12/1981 | Perlin . |
| 4,431,005 | 2/1984 | McCormick . |
| 4,444,195 | 4/1984 | Gold . |
| 4,499,493 | 2/1985 | Nishimura . |
| 4,522,212 | 6/1985 | Gelinas et al. . |
| 4,573,473 | 3/1986 | Hess . |
| 4,613,866 | 9/1986 | Blood . |
| 4,628,937 | 12/1986 | Hess et al. . |
| 4,649,924 | 3/1987 | Taccardi . |
| 4,697,595 | 10/1987 | Breyer et al. . |
| 4,699,147 | 10/1987 | Chilson et al. . |
| 4,706,681 | 11/1987 | Breyer et al. ........................... 128/642 |
| 4,777,955 | 10/1988 | Brayton et al. . |
| 4,812,976 | 3/1989 | Lundy . |
| 4,821,731 | 4/1989 | Martinelli et al. . |
| 4,899,750 | 2/1990 | Ekwall . |

(List continued on next page.)

FOREIGN PATENT DOCUMENTS

| | | |
|---|---|---|
| 0 152 905 | 8/1985 | European Pat. Off. . |
| 92301264 | 2/1992 | European Pat. Off. . |
| 0 591 899 | 10/1993 | European Pat. Off. . |
| 0728446A1 | 8/1996 | European Pat. Off. ........ A61B 19/00 |
| 3904914 | 8/1990 | Germany . |
| 41 19 150 | 12/1992 | Germany . |
| US94/08352 | 7/1994 | WIPO . |
| US94/11298 | 10/1994 | WIPO . |
| US95/01103 | 1/1995 | WIPO . |
| PCT/US95/ 07967 | 1/1996 | WIPO ............................ A61B 17/36 |
| PCT/CA96/ 00194 | 3/1996 | WIPO . |
| PCT/US95/ 11558 | 3/1996 | WIPO ............................ A61B 19/00 |

OTHER PUBLICATIONS

Meyer et al., Appliction of Sonomicrometry and Multidimensional Scaling to Cardiac Catheter Tracking, *Transactions on BioMedical Engineering*, vol. 44 No. 11, pp. 1061–1067, Nov. 1997.

Davis J.W., Improved Arrival Time Detection for Cardiac Pulse Transit Sonomicrometry, *Computers in Cardiology 1996*, pp. 145–459, 1996.

(List continued on next page.)

*Primary Examiner*—Marvin M. Lateef
*Assistant Examiner*—Shawna J. Shaw
*Attorney, Agent, or Firm*—Benesch, Friedlander, Coplan & Aronoff LLP

[57] ABSTRACT

A system for carrying out surgery on a bodily structure (e.g., breast and liver) with greater precision, accuracy, comfort and minimal invasiveness. A 3-dimensional tracking and imaging system (1000) is used to obtain an accurate position of an instrument as it is maneuvered by an operator, and to mark a location on the subject bodily structure. The system is particularly advantageous for surgical procedures for biopsying and destroying tumors in bodily structures which are easily deformable.

28 Claims, 7 Drawing Sheets

U.S. PATENT DOCUMENTS

| | | |
|---|---|---|
| 4,922,912 | 5/1990 | Watanabe . |
| 4,932,414 | 6/1990 | Coleman et al. .................. 128/600.09 |
| 4,940,064 | 7/1990 | Desai . |
| 4,945,305 | 7/1990 | Blood . |
| 5,000,190 | 3/1991 | Petre . |
| 5,012,814 | 5/1991 | Mills et al. . |
| 5,016,173 | 5/1991 | Kenet et al. ............................ 382/128 |
| 5,025,786 | 6/1991 | Siegel . |
| 5,041,973 | 8/1991 | Lebron et al. . |
| 5,042,486 | 8/1991 | Pfeiler et al. ........................... 128/653 |
| 5,054,492 | 10/1991 | Scribner et al. . |
| 5,054,496 | 10/1991 | Wen et al. . |
| 5,056,517 | 10/1991 | Fenici . |
| 5,081,993 | 1/1992 | Kitney et al. . |
| 5,104,393 | 4/1992 | Isner et al. . |
| 5,154,501 | 10/1992 | Svenson et al. . |
| 5,156,151 | 10/1992 | Imran . |
| 5,158,092 | 10/1992 | Glace . |
| 5,161,536 | 11/1992 | Vilkomerson et al. . |
| 5,172,699 | 12/1992 | Svenson et al. . |
| 5,220,924 | 6/1993 | Frazin . |
| 5,222,501 | 6/1993 | Ideker et al. . |
| 5,246,016 | 9/1993 | Lieber et al. . |
| 5,251,645 | 10/1993 | Fenn . |
| 5,260,985 | 11/1993 | Mosby . |
| 5,295,484 | 3/1994 | Marcus et al. . |
| 5,297,549 | 3/1994 | Beatty et al. . |
| 5,309,913 | 5/1994 | Kormos et al. ....................... 128/653.1 |
| 5,341,807 | 8/1994 | Nardella . |
| 5,357,956 | 10/1994 | Nardella . |
| 5,389,101 | 2/1995 | Heilbrun et al. . |
| 5,391,199 | 2/1995 | Ben-Haim . |
| 5,433,202 | 7/1995 | Mitchell et al. . |
| 5,443,489 | 8/1995 | Ben-Haim . |
| 5,469,847 | 11/1995 | Zinreich et al. . |
| 5,480,422 | 1/1996 | Ben-Haim . |
| 5,499,989 | 3/1996 | LaBash . |
| 5,515,853 | 5/1996 | Smith et al. ....................... 128/661.01 |
| 5,517,990 | 5/1996 | Kalfas et al. . |
| 5,546,951 | 8/1996 | Ben-Haim . |
| 5,568,811 | 10/1996 | Olstad . |
| 5,577,502 | 11/1996 | Darrow et al. . |
| 5,622,170 | 4/1997 | Schulz . |
| 5,662,111 | 9/1997 | Cosman . |
| 5,672,172 | 9/1997 | Zupkas . |
| 5,673,697 | 10/1997 | Bryan et al. . |
| 5,681,327 | 10/1997 | Heywang-Koebrunner . |
| 5,682,890 | 11/1997 | Kormos et al. . |
| 5,730,129 | 3/1998 | Darrow et al. . |
| 5,752,962 | 5/1998 | D'Urso . |
| 5,782,765 | 7/1998 | Jonkman . |

OTHER PUBLICATIONS

Morse, Wayne, Medical Electronics, *IEEE Spectrum*, pp. 99–102, Jan. 1997.

Josephson et al., Comparison of Endocardial Catheter Mapping with Intraoperative Mapping of Ventricular Tachycardia, *Circulation*, vol. 61, No. 2, pp. 395–404, 1980.

Josephson et al., Ventricular Tachycardia during Endocardial Pacing. II. Role of Pace–Mapping to Localize Origin of Ventricular Tachycardia, *The American Journal of Cardiology*, vol. 50, pp. 11–22, Jul. 1982.

Witkowski et al., An Automated Simultaneous Transmural Cardiac Mapping System, *American Journal of Physiology*, vol. 247, pp. H661–H668, 1984.

Fann et al., Endocardial Activation Mapping and Endocardial Pace–Mapping Using a Balloon Apparatus, *American Journal of Cardiology*, vol. 55, pp. 1076–1083, Apr. 1, 1985.

Tweddell et al., Potential Mapping in Septal Tachycardia: Evaluation of a New Intraoperative Mapping Technique; *Circulation*, vol. 80 (Supplement I), No. 3, pp. I–97–I–108, Sep. 1989.

Hauer et al., Endocardial Catheter Mapping: Wire Skeleton Techniques for Representation of Computed Arrhythmogenic Sites Compared with Intraoperative Mapping, *Circulation*, vol. 74. No. 6. pp. 1346–1354, Dec. 1986.

Pogwizd et al., Reentrant and Nonreentrant Mechanisms Contribute to Arrhythmogenesis During Early Myocardial Ischemia: Results Using Three–Dimensional Mapping, *Circulation Research*, vol. 61, No. 3, pp. 352–371, Sep. 1987.

Huang et al., Radiofrequency Catheter Ablation of the Left and Right Ventricles: Anatomic and Electrophysiologic Observations, *Pace*, vol. II, pp. 449–459, Apr. 1988.

Jackman et al., New Catheter Techniques for Recording Left Free–Wall Accessory Atrioventricular Pathway Activation, *Circulation*, vol. 78, No. 3, pp. 598–611, Sep. 1988.

Shenasa et al., Cardia Mapping, Part I: Wolff–Parkinson–White Syndrome, *Pace*, vol. 13, pp. 223–230, Feb. 1990.

Scheinman et al., Current Role of Catheter Ablative Procedures in Patients with Cardiac Arrhythmias, *Circulation*, vol. 83, No. 6, pp. 2146–2153, Jun. 1991.

Buckles et al., Computer–Enhanced Mapping of Activation Sequences in the Surgical Treatment of Supraventricular Arrhythmias, *Pace*, vol. 13, Pt. 1, pp. 1401–1407, Nov. 1990.

Tanigawa et al., Prolonged and Fractionated Right Atrial Electrograms During Sinus Rhythm in Patients with Paroxysmal Atrial Fibrillation and Sick Sinus Node Syndrome, *Journal of American College of Cardiologists*, vol. 17, No. 2, pp. 403–408, Feb. 1991.

Kaltenbrunner et al., Epicardial and Endocardial Mapping of Ventricular Tachycardia in Patients with Myocardial Infarction, *Circulation*, vol. 83, No. 3, pp. 1058–1071, Sep. 1991.

Masse et al., A Three–Dimensional Display for Cardiac Activation Mapping, *Pace*, vol. 14, Pt. 1, pp. 538–545, Apr. 1991.

Desai et al., Orthogonal Electrode Catheter Array for Mapping of Endocardial Focal Site of Ventricular Activation, *Pace*, vol. 14, Pt. 1, pp. 557–574, Apr. 1991.

Pollack et al., Intraoperative Identification of a Radiofrequency Lesion Allowing Validation of Catheter Mapping of Ventricular Tachycardia with a Computerized Balloon Mapping System, *Pace*, vol. 15, pp. 854–858, Jun. 1992.

Chen et al., Reappraisal of Electrical Cure of Atrioventricular Nodal Reentrant Tachycardia—Lesions from a Modified Catheter Albation Technique, *International Journal of Cardiology*, vol. 37, pp. 51–60, 1992.

Chen et al., Radiofrequency Catheter Albaltion For Treadment of Wolff–Parkinson–White Syndrome–Short–and Long–Term Follow–up, *International Journal of Cardiology*, vol. 37, pp. 199–207, 1992.

Scheinman, North American Society of Pacing and Electrophysiology (NASPE)Survey on Radiofrequency Catheter Ablation: Implications for Clinicians, Third Party Insurers, and Government Regulatory Agencies, *Pace*, vol. 15, pp. 2228–2231, Dec. 1992.

Silka et al., Phase Image Analysis of Anomalour Ventricular Activation in Petiatric Patients with Pre–excitation Syndromes or Ventricular Tachycardia, *American Heart Journal*, vol. 125, No. 2, Pt. 1, pp. 372–380, Feb. 1993.

Josephson, Clinical Cardiac Electrophysiology: Techniques and Interpretations, 2nd Ed., pp. 566–580, 608–615, 770–783, *Lea & Febiger*, Malvern, Pa., 1993.

Holt et al., Ventricular Arrhythmias—A Guide to Their Localization, *British Heart Journal*, vol. 53, pp. 417–430, 1985.

Joseph et al., Role of Catheter Mapping in the Preoperative Evaluation of Ventricular Tachycardia, *American Journal of Cardiology*, vol. 40, pp. 207–220, Jan. 1982.

Kucher et al., Electrocardiographic Localization of the site of Ventricular Tachycardia in Patients with Prior Myocardial Infarction, *JACC*, vol. 13, No.4 pp. 893–900.

Page, Surgical Treatment of Ventricular Tachycardia: Regional Cryoablation Guided by Computerized Epicardial and Endocardial Mapping, *Circulation*, vol. 80, (Supplement I), No. 3, pp. I124–I–134, Sep. 1989.

SYSTEM FOR CARRYING OUT SURGERY, BIOPSY AND ABLATION OF A TUMOR OR OTHER PHYSICAL ANOMALY

This is a continuation-in-part of International Application Ser. No. PCT/CA96/00194, filed on Mar. 24, 1996 and which designated the U.S., which is a CIP of Ser. No. 08/411,959 filed Mar. 28, 1995, now U.S. Pat. No. 5,515,853.

FIELD OF INVENTION

The present invention relates generally to a system for carrying out a surgical procedure on a bodily structure (e.g., breast, liver, pancreas, kidney, uterus or other solid organ), and more particularly to a system for tracking an instrument within a bodily structure, marking the location of a tumor, and biopsying or destroying the tumor.

BACKGROUND OF THE INVENTION

Breast biopsies are currently performed using a device known as a Core Biopsy System. The Core Biopsy system first obtains a stereo-mammogram from a patient's breast, while the breast is immobilized by being compressed between two plates, and uses these two images to calculate the 3-D coordinates of the suspected tumor. A needle is then fired into the breast and a biopsy is taken of the suspected tumor. If the biopsy is positive, then the patient is scheduled for tumor removal surgery. It should be noted that before the biopsy procedure is commenced, the tumor needs to be manually identified by a radiologist.

The surgical procedure generally proceeds in the following manner. A patient undergoes multi-plane mammography, a radiologist examines the film, and then inserts a wire into the breast so that it punctures the tumor. This procedure is visualized using repetitive x-ray imaging. More recently, the stereotactic breast imaging system has been used to localize the tumor more precisely and assist in the insertion of the wire. The patient is then sent to the operating room, and the breast is prepared for surgery by the application of a topical sterilant. The surgeon then cuts the breast open, following the wire until the lesion is found and excised.

One of the undesirable factors of the foregoing procedure is the presence of a long wire through the breast for many hours at a time while awaiting surgery. This is highly traumatic for the patient and undesirable. Secondly, during surgery, the surgeon must follow the wire into the breast. Since this may not be the optimal trajectory, the surgeon would ideally like to plan the entry pathway independent of the wire, or eliminate the wire altogether. This can be done only if the location of the lesion within the breast can be identified using a system that takes into account the inherent deformability of the breast tissue. It should be appreciated that the problem associated with the deformability of breast tissue applies equally to other easily deformable bodily structures such as the liver.

The current problem limiting use of stereotactic breast surgery is the large difference between the position and shape of the breast during mammography and surgery. In this regard, images taken during mammography become unusable for stereotactic positioning during the surgical procedure. While stereotactic surgery can be done with the breast compressed, and the patient lying on the stereotactic table, this is not desirable. The ideal way to do this surgery is with the patient on her back, as is done routinely.

The present invention overcomes these and other drawbacks of prior art systems and provides a system having significantly improved accuracy and providing greater comfort to the patient.

SUMMARY OF THE INVENTION

According to the present invention there is provided a system for performing stereotactic surgery with improved accuracy and comfort.

It is an object of the present invention to provide a system for performing surgery on a bodily structure in a minimally invasive manner.

It is another object of the present invention to provide a system for performing surgery on a bodily structure which is inherently deformable.

It is another object of the present invention to provide a system for performing surgery, wherein there is increased precision of the localization of a tumor, enabling more precise surgery.

It is still another object of the present invention to provide a system for performing surgery, wherein a constant 3-D reference frame is established.

It is still another object of the present invention to provide a system for performing surgery, wherein deformation of the subject bodily structure does not alter a 3-D frame of reference.

It is yet another object of the present invention to provide a system for performing breast surgery in which there is greatly reduced potential for disfiguring or altering the shape of the breast.

It is yet another object of the present invention to provide a system for performing surgery of the liver, or other internal organ, in which there is more accurate locating of a tumor.

It is yet another object of the present invention to provide a system for performing surgery of the liver, or other organ, in which there is a need for more accurate locating of a surgical instrument.

Still other objects and advantages of the invention will become apparent to those skilled in the art upon a reading and understanding of the following detailed description, accompanying drawings and appended claims.

BRIEF DESCRIPTION OF THE DRAWINGS

The invention may take physical form in certain parts and arrangements of parts, a preferred embodiment and method of which will be described in detail in this specification and illustrated in the accompanying drawings which form a part hereof, and wherein.

DETAILED DESCRIPTION OF THE PREFERRED EMBODIMENT

It is known that using the time-of-flight principle of high frequency sound waves, it is possible to accurately measure distances within an aqueous medium, such as inside the body of a living being during a surgical procedure. High frequency sound, or ultrasound, is defined as vibrational energy that ranges in frequency from 100 kHz to 10 MHz. The device used to obtain three-dimensional measurements using sound waves is known as a sonomicrometer. Typically, a sonomicrometer consists of a pair of piezoelectric transducers (i.e., one transducer acts as a transmitter while the other transducer acts as a receiver). The transducers are implanted into a medium, and connected to electronic circuitry. To measure the distance between the transducers, the transmitter is electrically energized to produce ultrasound. The resulting sound wave then propagates through the medium until it is detected by the receiver.

The transmitter typically takes the form of a piezoelectric crystal that is energized by a high voltage spike, or impulse function lasting under a microsecond. This causes the piezoelectric crystal to oscillate at its own characteristic resonant frequency. The envelope of the transmitter signal decays rapidly with time, usually producing a train of six or more cycles that propagate away from the transmitter through the aqueous medium. The sound energy also attenuates with every interface that it encounters.

The receiver also typically takes the form of a piezoelectric crystal (with similar characteristics to the transmitter piezoelectric crystal) that detects the sound energy produced by the transmitter and begins to vibrate in response thereto. This vibration produces an electronic signal in the order of millivolts, that can be amplified by appropriate receiver circuitry.

The propagation velocity of ultrasound in an aqueous medium is well documented. The distance traveled by a pulse of ultrasound can therefore be measured simply by recording the time delay between the instant the sound is transmitted and when it is received. Three-dimensional coordinates can be determined from the distance measurement.

Figure 1:
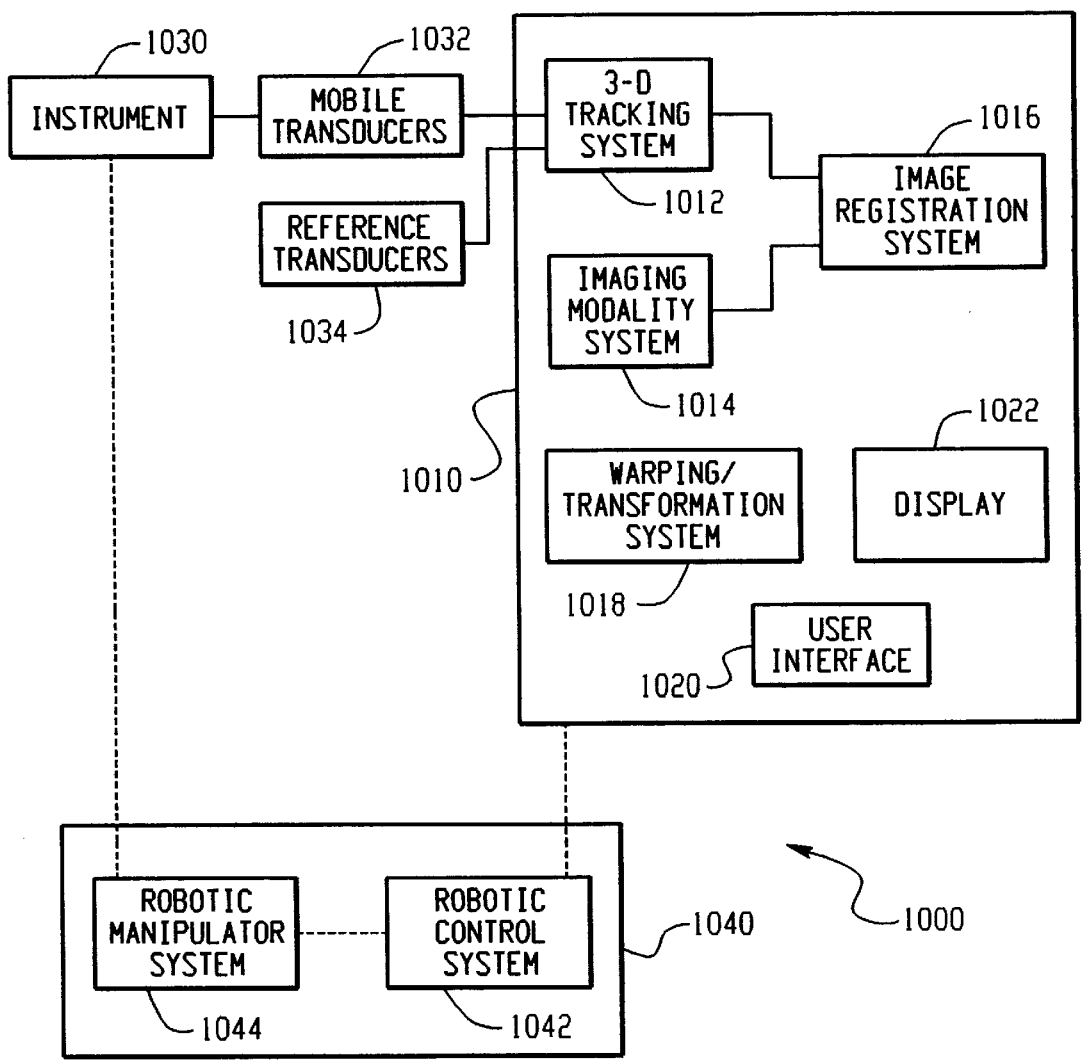
FIG. 1 shows a 3-dimensional tracking and imaging system according to a preferred embodiment of the present invention.

Referring now to the drawings wherein the showings are for the purposes of illustrating a preferred embodiment of the invention only and not for purposes of limiting same, FIG. 1 shows a three-dimensional (3-D) tracking and imaging system 1000 for use in connection with the procedure of the present invention. 3-D tracking and imaging system 1000 is generally comprised of a computer system 1010, mobile transducers 1032, reference transducers 1034, an instrument 1030 and an optional robotics subsystem 1040.

Computer system 1010 is generally comprised of a 3-D tracking system 1012, an imaging modality system 1014, an image registration system 1016, a warping and geometry transformation system 1018 ("warp system"), a user interface 1020 and a display 1022. It should be appreciated that 3-D tracking system 1012 may take the form of a sound-based system or an electromagnetic-based system. Both time of flight and phase relationships may be used to determine distance. Preferably, 3-D tracking system 1012 takes the form of the 3-D ultrasound tracking system described in U.S. Pat. No. 5,515,853 and PCT Application Ser. No. PCT/CA96/00194, both of which are incorporated herein by reference.

Instrument 1030 may take the form of a catheter, a probe (e.g., a cryoprobe), a sensor, a needle, a scalpel, a forceps or other device or instrument used in a surgical or diagnostic procedure. Mobile transducers 1032 and reference transducers 1034 may take the form of an ultrasonic transducer or an electronic transducer. However, for purpose of illustrating a preferred embodiment of the present invention, transducers 1032 and 1034 will take the form of ultrasonic transducers (i.e., piezoelectric crystals).

A plurality of mobile transducers 1032 are fitted to instrument 1030. One or more reference transducers 1034 provide a reference position relative to mobile transducers 1032. In this respect, reference transducers 1034 may be located to provide an internal reference frame inside a patient's body or on the surface of a patient body to provide an external reference frame.

As indicated above, reference transducers 1034 may be transmitters, transceivers or receivers that can generate ultrasound or electromagnetic radiation, that can be detected by mobile transducers 1032.

3-D tracking system 1012 transforms the multiple distance measurements between all of the transducers 1032, 1034 into XYZ coordinates relative to a referenced axis, as described in detail above. It should be appreciated that the reference frame provided by reference transducers 1034 must be self-determining, that is, if the reference frame becomes distorted, this distortion needs to be detected by reference transducers 1034. Detection is typically done by using transceivers that can determine the distance between any combination of two transducers, and hence their relative spacial coordinates in 3-D space. In this regard, the position of the transducers is obtained in 3-D from the images acquired of the bodily structure (e.g., tissue or organ) that show "dots" where the transducers are located, and also from the transducers themselves when they are in the bodily structure. If there is some discrepancy in the distances between all combinations of transducers, then the bodily structure must have deformed (i.e., "warped") after the images were acquired. A mathematical coordinate transformation can be used to specify exactly how to correct the image set and account for the warping. The distance between any combination of two transducers is determined by having each transducer send a signal to all other transducers. In this way, all the distances between the transducers are known. From these distances, XYZ coordinates can be calculated, in reference to some transducer as the origin.

Imaging modality system 1014 acquires 2-D, 3-D or 4-D image data sets from an imaging source, such as fluoroscopy, an MRI (magnetic resonance imaging), CT (computerized tomography) or 2-D or 3-D ultrasound device, to provide a "template" through or against which the shape, position and movement of instrument 1030 being tracked can be displayed. The template typically takes the form of an image of the environment surrounding the instrument (e.g., a bodily structure). It should be noted that if multiple (3-D) volumes are acquired at different time intervals, a 4-D image is obtained (i.e., 3-D image changing over time).

Image registration system 1016 registers the position of instrument 1030 within the spatial coordinates of the image data set provided by imaging modality system 1014. The position of instrument 1030 is provided by the 3-D tracking system 1012. Image registration system 1016 will provide a display of instrument 1030 at its proper 3-D location inside the bodily structure and orientation relative to the bodily structure itself. It should be appreciated that registration system 1016 may be user assisted, or completely automated if image processing algorithms are implemented to automatically detect the spacial locations of the transducers (typically the reference transducers) in the image data set.

Warp system 1018 is a software-based system that transforms or "warps" the image data sets by the appropriate values to correspond to a deformation that has occurred in the reference frame between the time that the image data set were acquired and the time that the procedure is to be implemented during surgery. Accordingly, warp system 1018 is typically comprised of a matrix transformation routine that maps the deformed geometry onto the original image data set, and distorts it appropriately.

User interface 1020 enables a user to interact with computer system 1010, including programming computer system 1010 to perform a desired function. For example, a particular view for display can be selected. Instruments 1030 (e.g., probes or catheters) can be activated using user interface 1020. Display 1022 displays to the user registered images provided by image registration system 1016.

Optional robotics system 1040 is generally comprised of a robotics control system 1042 and a robotic manipulator system 1044. Robotics control system 1042 controls robotic manipulator system 1044 to follow a programmed path that can be appropriately changed, based on shifting, warping or changes in the shape of a bodily structure at the time of surgery. Robotic manipulator system 1044 physically moves instrument 1030 as instructed by robotic control system 1042.

The above-described 3-D tracking and imaging system 1000 can be used to provide both stereotactic localization during biopsy and surgery that is more interactive than existing stereotaxy table systems, and tagging of a tumor so that it can subsequently be localized during conventional surgery. It should be appreciated that while the present invention is described with reference to the biopsy and ablation of a tumor, it is also suitable for use in connection with other physical anomalies.

Figure 2:
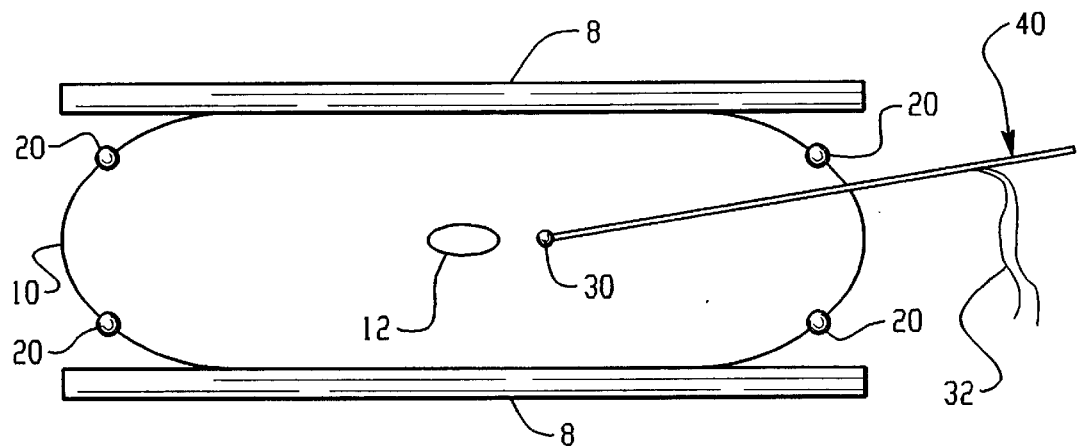
FIG. 2 shows a breast having a reference transducer deposited therein while the breast is under compression.

Tagging of a tumor located in a breast will now be described with reference to FIG. 2. A plurality of external reference transducers 20 are affixed to the surface of breast 10. Reference transducers 20 provide a stereotactic external reference frame for the interactive 3-D display of the movement of probe 40 during insertion of internal transducer 30, as will be described below. Tumor 12 is tagged by inserting internal ultrasonic transducer 30 into tumor 12 during conventional mammography, wherein breast 10 is placed under compression by the use of compression plates 8. Transducer 30 takes the place of the localizer needle that is presently inserted into the tumor according to prior art methods.

Figure 3:
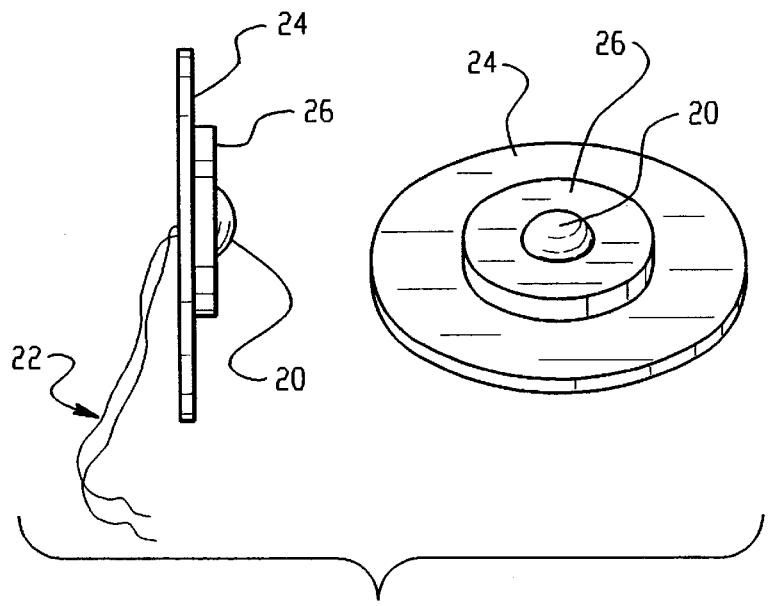
FIG. 3 shows a transducer arrangement according to a preferred embodiment of the present invention.

Reference transducers 20 may take the form of individual stick-on elements, or part of an adhesive strip. FIG. 3 shows an exemplary embodiment of an arrangement for affixing reference transducer 20 using an adhesive. Reference transducer 20 is supported by an adhesive patch 24. A matching gel 26 is applied to the adhesive patch 24 and reference transducer 20 is arranged therein. Gel 26 provides acoustic coupling. Electrical leads 22 of reference transducer 20 exit through an opening in adhesive patch 24.

Figure 4A:
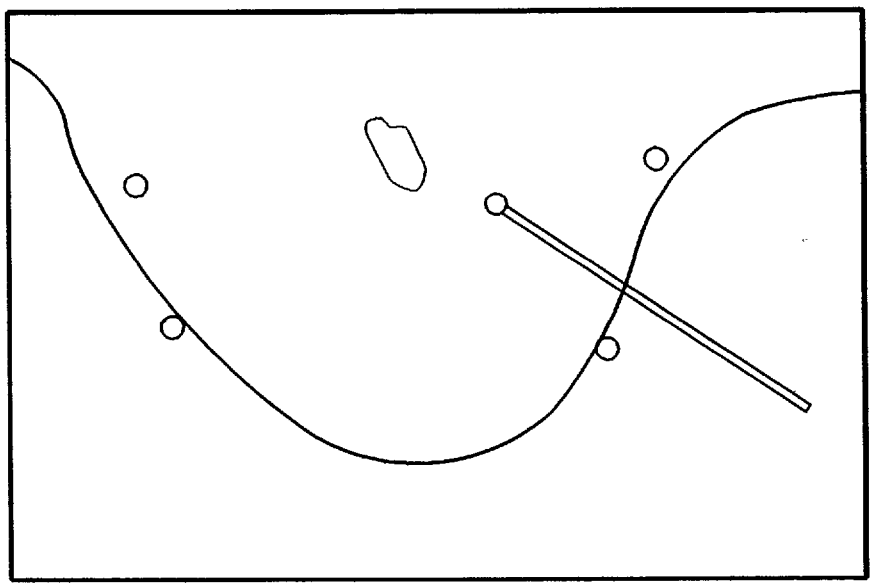
FIGS. 4A and 4B illustrates the progression of a probe through a breast shown against the original stereo mammograms.
Figure 4B:
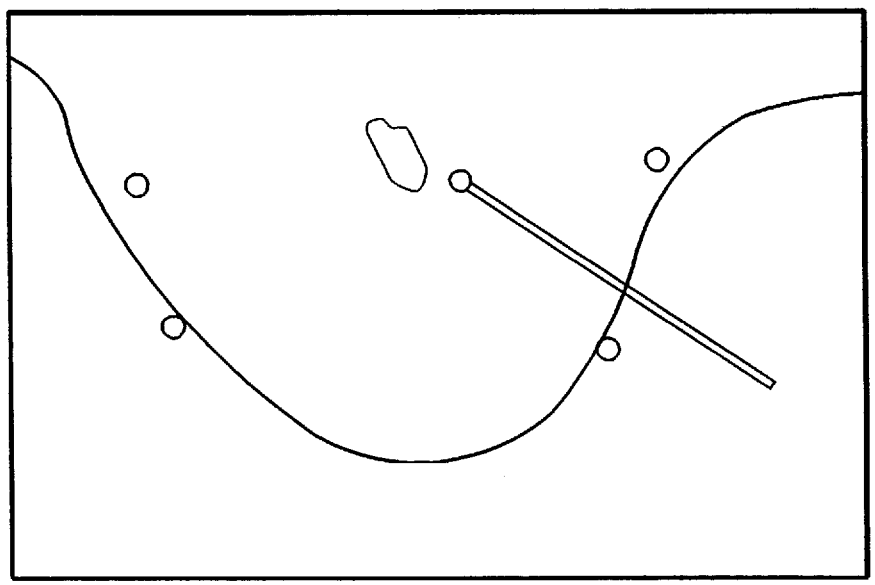

It should be appreciated that reference transducers 20 will appear on the two mammograms obtained from at two slightly different angles, and can be used to generate fiducial markers for the stereographic determination of 3-D coordinates of tumor 12, relative to these markers. Moreover, the motion of probe 40 can also be referenced against these bi-plane mammograms using transducer 30. Accordingly, a user can track the motion of probe 40 both in a 3-D viewing environment, as well as against the original radiograms, during the deposition of transducer 30, which will act as a "homing beacon" for the tumor during subsequent biopsy or surgery. The progression of an instrument through a breast is shown against mammograms in FIGS. 4A and 4B.

Once transducer 30 has been deposited in tumor 12, and probe 40 removed from the breast 10, the patient can comfortably walk around, since electrical leads 32 connected to transducer 30 are very flexible, and can be taped to the patient's skin. It should be appreciated that transducer 30 can reliably denote the location of tumor 12 during subsequent surgery since it remains lodged in tumor 12 by means of small barbs that deploy during insertion.

The foregoing approach is a significant improvement over conventional stereotaxy. Since a tremendous change occurs in the shape of the breast between mammography and surgery, the tumor may be in a completely different location than previously perceived during mammography. As a result, any stereotactic registration of external breast shape with the internal breast images is lost. However, since the tumor is tagged with transducer 30, its location can always be determined during subsequent procedures.

After the foregoing procedure, the patient goes to the operating room, the breast is prepared for surgery, and new adhesive, with ultrasonic transducers imbedded therein, are attached to the skin. Transducers 20 and 30 are connected to the 3-D tracking and imaging system described above. It should be appreciated that transducers 20 and 30 enable the tracking of additional transducers that may be inserted into the breast during subsequent surgery.

Figure 5A:
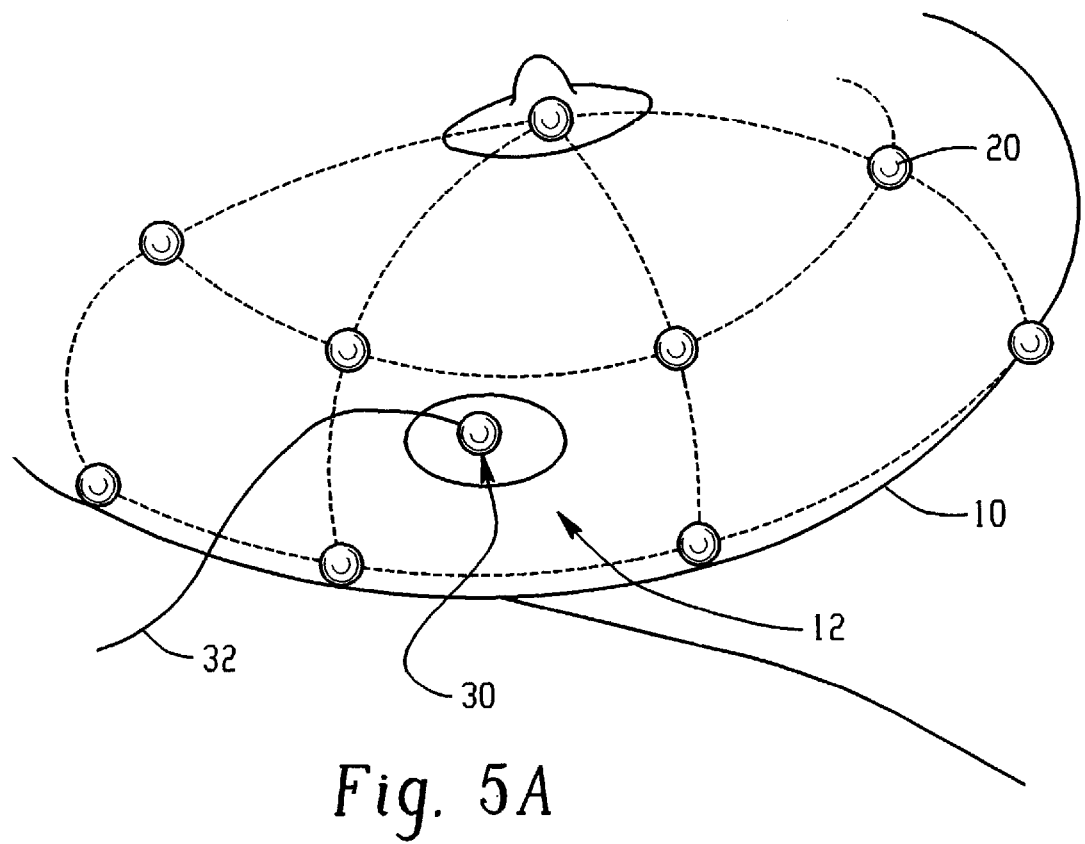
FIG. 5A shows reference transducers and a "homing beacon" transducer located on a breast.
Figure 5B:
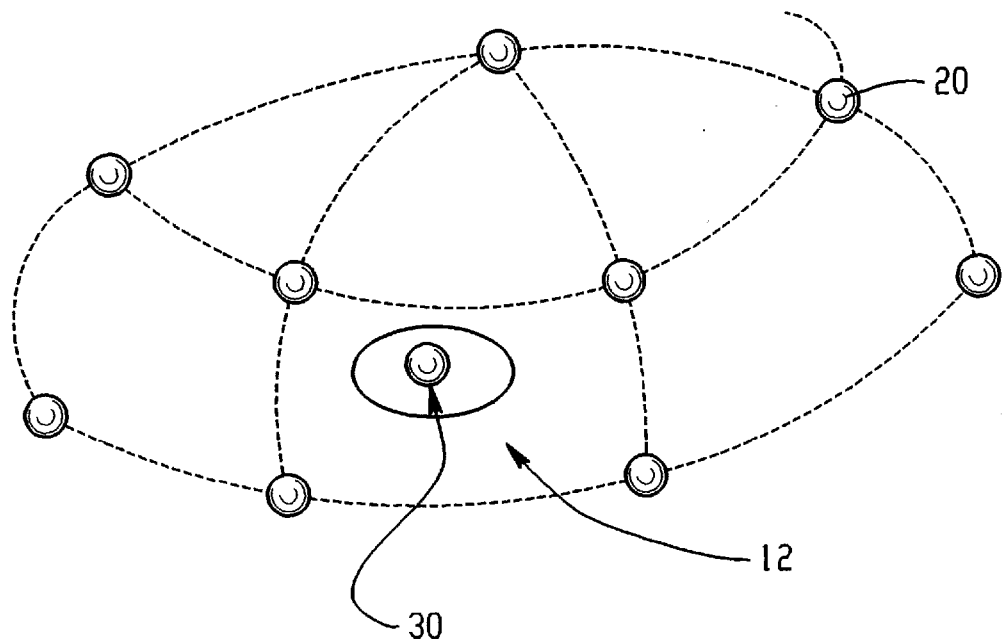
FIG. 5B shows the scene of FIG. 5A, as shown in 3-D on a display unit.

FIG. 5A shows breast 10 having tumor 12 tagged with internal transducer 30. The attachment of external reference transducers 20 and the presence of internal transducer 30 in tumor 12 enables the generation of a 3-D viewing environment within which tumor 12 can be localized relative to breast 10 (FIG. 5B). This means of visualizing the spatial location of tumor 12 relative to the outside of breast 10 is important in planning the tumor removal surgery. The conventional technique is to simply follow a previously inserted wire into the breast. This is not desirable since it may not be the most cosmetically desirable path to take. By analyzing a 3-D display, such as shown in FIG. 5B, a surgeon can decide from which direction to begin incisions.

Figure 6A:
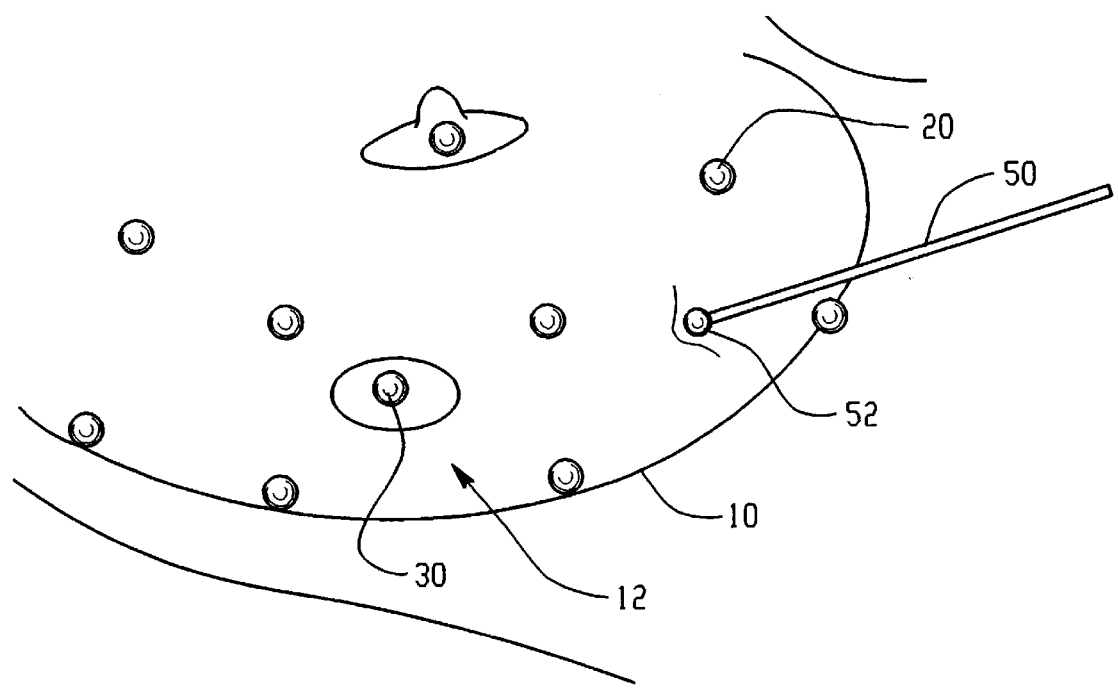
FIG. 6A shows a probe having a transducer in contact with the breast shown in FIG. 4A.
Figure 6B:
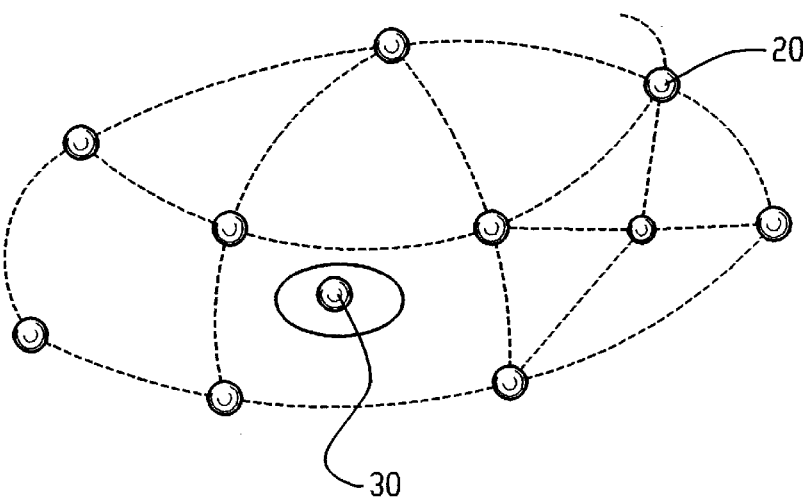
FIG. 6B shows the scene of FIG. 6A, as shown in 3-D on a display unit.

As the incisions are made, a secondary probe 50 can be touched into the wound to determine if the trajectory should be modified. FIG. 6A shows probe 50 touching breast 10. It should be noted that probe 50 has a transducer 52 arranged on its tip. Accordingly, a 3-D display as shown in FIG. 6B can be generated. Once transducer 52 mounted to probe 50 comes into contact with the tissue, it will appear in the 3-D display and can be localized relative to transducer 30 (i.e.,"homing beacon"). Accordingly, the 3-D display allows the surgical path to be visualized and corrected, as necessary. Because the external reference frame formed by reference transducers 20 is affixed to the external surface of breast 10, it does not matter if the breast tissue deforms following mammogram imaging. In this regard, transducer 30 will always be shown relative to the new configuration of transducers 20 affixed to the external surface of breast 10. Moreover, since external reference transducers 20 communicate with each other, they will set up a new, changing coordinate frame regardless to what extent the breast tissue is manipulated. In each case, the relative position of transducer 30 is displayed within this coordinate system.

The foregoing approach provides numerous advantages and overcomes the current limitations of stereotactic surgery that is based on a fixed coordinate system. With regard to clinical advantages, breast surgery can be done much less invasively. When developed further, it may be possible to remove tumors in a much less invasive way, by inserting small catheters that ablate, suction or in some other way destroy the tumor without having to open up the breast for visual inspection. This will greatly reduce the potential for disfiguring or altering the shape of the breast. Another important clinical advantage is the increased precision of the localization of the tumor, enabling more precise surgery. The theoretical precision of the 3-D tracking system described above is 20 µm. In practice, the 3-D spatial precision is less than 1 mm, and due to geometrical transformation errors, this may rise to 2 mm. This is apparently still better than the precision currently available using the wire insertion technique or conventional stereotactic tables. Such increased precision will improve the success rate of tumor excision, without the need for larger, more radical lumpectomies. Yet another clinical advantage is that the foregoing procedure can be readily applied to both biopsies, open surgery or fully closed, minimally invasive surgery. It provides a real-time, user assisted means of approaching tumors inside the breast and is much less costly than conventional stereotactic equipment.

Figure 7:
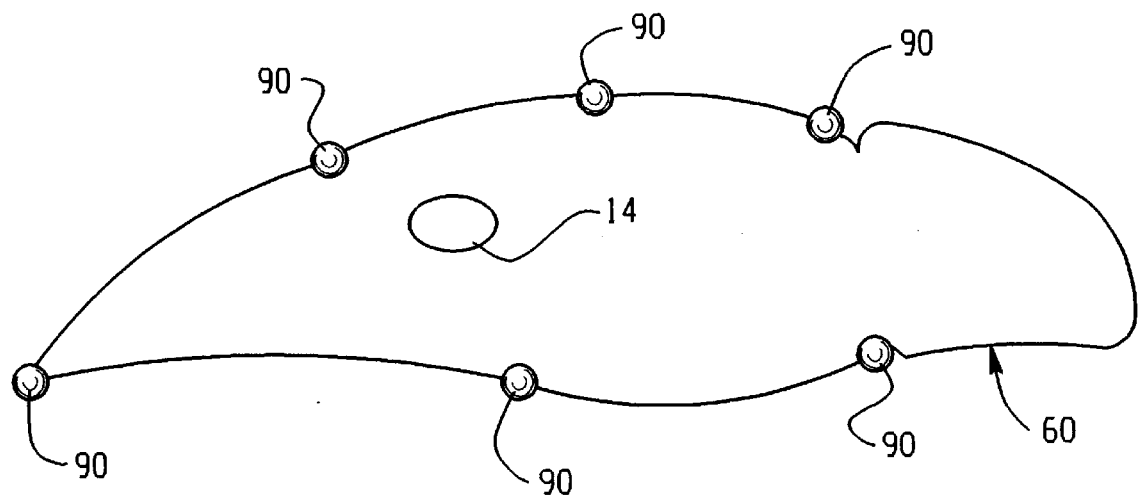
FIG. 7 shows a liver having a plurality of reference transducers applied thereto.
Figure 8:
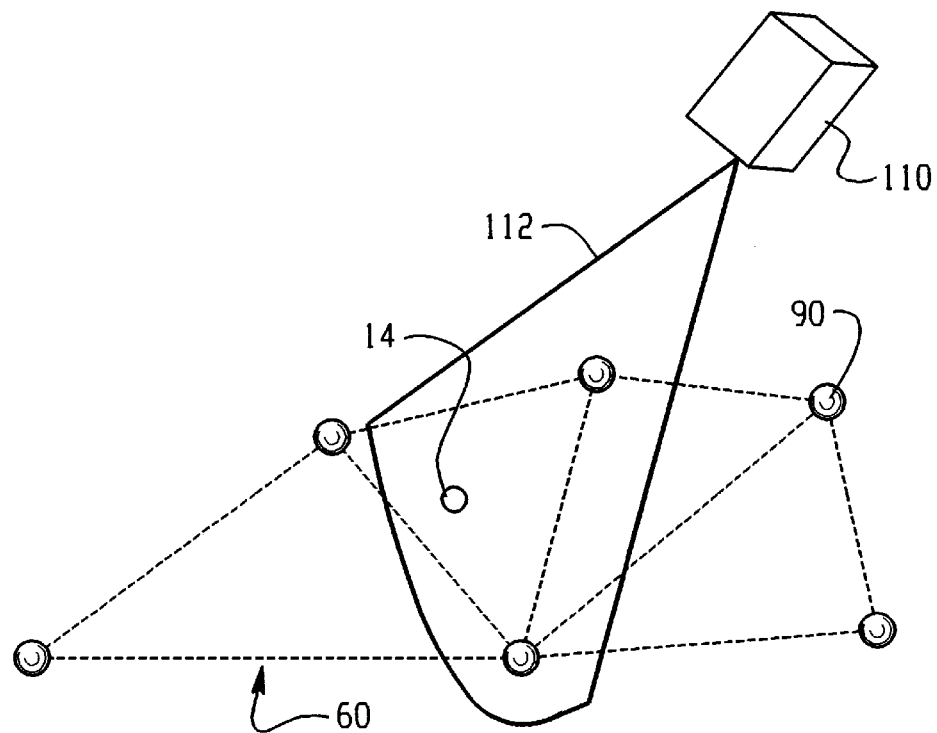
FIG. 8 illustrates a procedure for generating a 3-D scene including a 2-D ultrasound image of the liver shown in FIG. 7.

The present invention may also be used to locate an instrument at a tumor site, according to another embodiment of the present invention. FIG. 7 shows a liver 60 having a tumor 14. A 3-dimensional reference frame of liver 60 is established by attaching a plurality of reference transducers 90 to the external surface of liver 60. In this regard, transducers 90 may be attached under laparoscopic guidance. Next, the location of tumor 14 is determined using guided 2-dimensional ultrasound 110, which generates a 2-D ultrasound imaging plane 112. A 2-D ultrasound imaging plane is displayed within the 3-D reference frame to form a 3-D scene. When tumor 14 is transected by ultrasound imaging plane 112, the user places a cursor mark in the 3-D scene to identify the center of tumor 14. The 3-D tracking and imaging system determines the 3-D coordinates of tumor 14 within the 3-D scene, relative to the 3-D reference frame established by transducers 90. It should be appreciated that since transducers 90 are fixed to liver 60, the location of tumor 14 remains fixed relative to the 3-D reference frame, even as liver 60 itself is manipulated causing deformation of liver 60.

Figure 9:
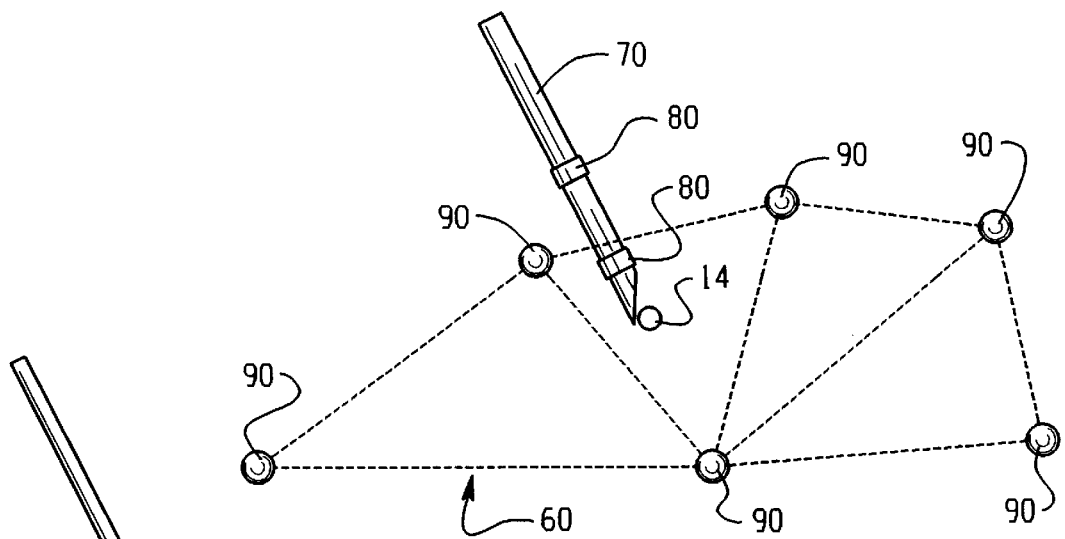
FIG. 9 shows insertion of a locatable tube into the liver shown in FIG. 7.
Figure 10:
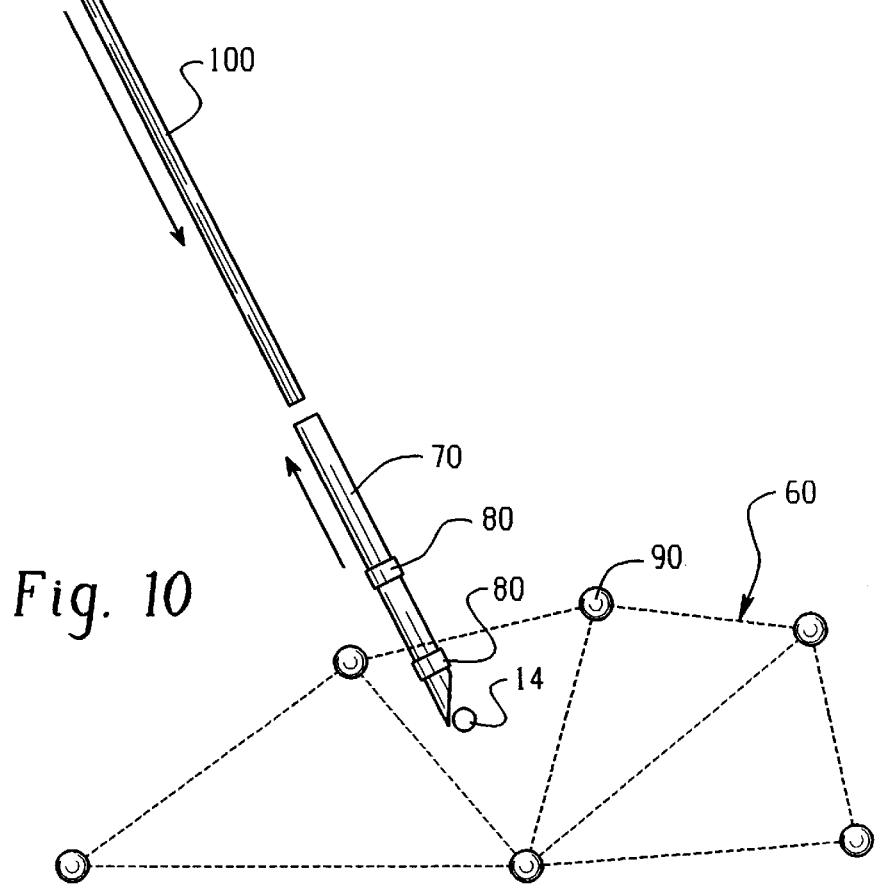
FIG. 10 shows the insertion of a cryoprobe into a trackable sleeve located at the site of a tumor.

Referring now to FIGS. 9 and 10 a cryoprobe 100 (or other instrument) is located at tumor 14. In this respect, an ultrasonically locatable sheath attachment 70 is inserted into liver 60 and positioned such that its end corresponds to the location of tumor 14. Sheath attachment 70 preferably takes the form of a hollow rigid sleeve or tube having transducers 80 mounted thereto. A preferred sheath attachment 70 is described in detail in co-pending U.S. application Ser. No. 08/812,249, entitled "Tracking Data Sheath", filed Mar. 7, 1997, and incorporated herein by reference. Transducers 80 allow the position of sheath attachment 70 to be tracked using the 3-D tracking and imaging system, described above.

Once sheath attachment 70 has been located at the site of tumor 14, cryoprobe 100 is inserted into sheath attachment 70, such that it stops at the mouth of the sheath. Accordingly, cryoprobe 100 does not require physical modifications to be located at the site of tumor 14. Next, sheath attachment 70 is pulled back along the shaft of cryoprobe 100. Thereafter, cryoprobe 100 is energized to ablate tumor 14 in a well known manner.

Alternatively, the foregoing procedure can be performed by inserting a trackable blunt guide instrument having ultrasonic transducers mounted thereto and locating the guide instrument at the site of the tumor. Next, a tube or sleeve is placed at the site of the tumor by placing the tube over the guide instrument. Then, the guide instrument is removed, leaving just the sleeve. A cryoprobe (or other instrument) is then inserted through the sleeve, thus locating the cryoprobe at the site of the tumor.

The invention has been described with reference to a preferred embodiment. Obviously, modifications and alterations will occur to others upon a reading and understanding of this specification. It is intended that all such modifications and alterations be included insofar as they come within the scope of the appended claims or the equivalents thereof.

Having thus described the invention, it is now claimed:

1. A method for carrying out surgery on a tumor in a bodily structure for the purpose of biopsy or ablation, comprising:

mounting a plurality of reference transducer means to fixed positions relative to a bodily structure to provide a reference frame;

obtaining a template image of the bodily structure;

registering the reference frame with the template image to obtain a 3-dimensional scene;

locating a beacon transducer means at the location of a tumor by displaying the position of the beacon transducer means within the 3-dimensional scene;

fixing the beacon transducer means at the location of the tumor to identify the location thereof; and locating a first instrument means at the location of the tumor by displaying the position of the first instrument means relative to the reference frame and beacon transducer means.

2. A method according to claim 1, wherein said step of mounting a plurality of reference transducer means to fixed positions includes the step of mounting a plurality of transducer means to the surface of a breast.

3. A method according to claim 1, wherein the step of mounting a plurality of reference transducer means to fixed positions includes the step of mounting a plurality of transducer means to the external surface of a solid organ.

4. A method according to claim 1, wherein said step of obtaining a template image includes obtaining a mammogram.

5. A method according to claim 1, wherein said step of obtaining a template image includes obtaining a radiological image.

6. A method according to claim 1, wherein the step of locating the beacon transducer means at the location of the tumor includes the steps of:

attaching the beacon transducer means to a second instrument means;

moving the second instrument means to the location of the tumor;

detaching the beacon transducer means from the second instrument means; and fixing the beacon transducer means at the location of the tumor.

7. A system for carrying out surgery on a tumor in a bodily structure for the purpose of biopsy or ablation, comprising:

a plurality of reference transducer means located at fixed positions on the bodily structure to provide a reference frame;

means for obtaining a template image of a bodily structure;

registration means for registering the reference frame with the template image to obtain a 3-dimensional scene;

display means for displaying the 3-dimensional scene of the bodily structure;

first instrument means for fixing the location of a beacon transducer means at the site of a tumor to identify the location of the tumor; and second instrument means for performing a surgical procedure at the site of the tumor, wherein the second instrument means has a transducer means for indicating the position of the first instrument means relative to the reference frame and the location of the beacon transducer means.

8. A system according to claim 7, wherein said fixed positions are on the surface of a breast.

9. A system according to claim 7, wherein said fixed positions are on the external surface of a solid organ.

10. A system according to claim 7, wherein said template image is a mammogram.

11. A system according to claim 7, wherein said template image is a radiological image.

12. A system according to claim 7, wherein said first instrument means includes means for separating said beacon transducer means from said first instrument means.

13. A system according to claim 7, wherein each of said plurality of reference transducer means comprises:

a transducer device; and support means for supporting the transducer device, said support means including an adhesive for affixing the reference transducer means to the fixed position on the bodily structure and a gel for acoustic coupling.

14. A system according to claim 13, wherein said transducer device includes a piezoelectric material transducer.

15. A method for carrying out surgery on a tumor in a bodily structure for the purpose of biopsy or ablation, comprising:

mounting a plurality of reference transducer means to fixed positions on a bodily structure to provide a reference frame;

obtaining a template image of the bodily structure;

registering the reference frame with the template image to obtain a 3-dimensional scene;

locating a trackable sleeve means at a location of the tumor by displaying the position of the sleeve means within the 3-dimensional scene; and locating a first instrument means at the location of the tumor by positioning the first instrument means within the sleeve means.

16. A method according to claim 15, wherein the step of mounting a plurality of transducer means to fixed positions includes the step of mounting a plurality of transducer means to a solid organ under laparoscopic guidance.

17. A method according to claim 15, wherein said template image is a 2-dimensional ultrasound image.

18. A method according to claim 15, wherein said method further comprises the step of displaying a reference mark in the 3-dimensional scene, at the location of the tumor to facilitate locating the trackable sleeve means at the location of the tumor.

19. A method according to claim 15, wherein the method further includes the step of removing the trackable sleeve from the first instrument means.

20. A system for carrying out surgery on an anomaly in a bodily structure for the purpose of biopsy or ablation, comprising:

a plurality of reference transducer means mounted at fixed positions on a bodily structure to provide a reference frame;

means for obtaining a template image of the bodily structure;

registration means for registering the reference frame with the template image to obtain a 3-dimensional scene;

trackable sleeve means locatable relative to an associated anomaly to identify a location of a associated anomaly;

display means adapted for displaying the position of the trackable sleeve means within the 3-dimensional scene to locate the sleeve means at the location of the associated anomaly; and first instrument means adapted for performing a surgical procedure at the location of the associated anomaly, the first instrument means located at the location of the associated anomaly by positioning the first instrument means within the sleeve means.

21. A system according to claim 20, wherein said fixed positions are located on an external surface of a solid organ.

22. A system according to claim 20, wherein said template image is a 2-dimensional ultrasound image.

23. A system according to claim 20, wherein said system further comprises means for displaying a reference mark in the 3-dimensional scene at the location of the associated anomaly to facilitate locating the trackable sleeve means at the location of the associated anomaly.

24. A system according to claim 20, wherein said first instrument means is a cryoprobe.

25. A method for carrying out surgery on a tumor in a bodily structure for the purpose of biopsy or ablation, comprising:

mounting a plurality of reference transducer means to a solid organ to provide a reference frame defining the position of the solid organ;

obtaining a template image of a bodily structure;

registering the reference frame with the template image to obtain a 3-dimensional scene;

locating a trackable instrument means at the location of a tumor by displaying the position of the trackable instrument means within the 3-dimensional scene;

arranging a sleeve means over the trackable instrument means;

removing the trackable instrument means from the sleeve means; and inserting a second instrument means into the sleeve means.

26. A system according to claim 25, wherein said step of inserting a second instrument means into the trackable sleeve means includes inserting an ablation means into the trackable sleeve means.

27. A system for carrying out surgery on a tumor in a bodily structure for the purpose of biopsy or ablation, comprising:

a plurality of reference transducer means located at fixed positions on the bodily structure to provide a reference frame, wherein said plurality of reference transducer means include:

a transducer device, and support means for supporting the transducer device, said support means including an adhesive for affixing the transducer device to the fixed position on the bodily structure and a gel for acoustic coupling;

means for obtaining a template image of a bodily structure;

registration means for registering the reference frame with the template image to obtain a 3-dimensional scene;

display means for displaying the 3-dimensional scene of the bodily structure;

first instrument means for fixing the location of a beacon transducer means at the site of a tumor to identify the location of the tumor; and second instrument means for performing a surgical procedure at the site of the tumor, wherein the second instrument means has a transducer means for indicating the position of the first instrument means relative to the reference frame and the location of the beacon transducer means.

28. A method for carrying out surgery on a physical anomaly in a bodily structure for the purpose of biopsy or ablation, comprising:

mounting a plurality of reference transducer means to fixed positions relative to a bodily structure to provide a reference frame;

obtaining a template image of the bodily structure;

registering the reference frame with the template image to obtain a 3-dimensional scene;

locating a beacon transducer means at the location of a physical anomaly by displaying the position of the beacon transducer means within the 3-dimensional scene;

fixing the beacon transducer means at the location of the physical anomaly to identify the location thereof; and locating a first instrument means at the location of the physical anomaly by displaying the position of the first instrument means relative to the reference frame and beacon transducer means.

* * * * *